(12) United States Patent
Thompson-Nauman et al.

(10) Patent No.: US 11,986,648 B2
(45) Date of Patent: *May 21, 2024

(54) DEVICES AND TECHNIQUES FOR ANCHORING AN IMPLANTABLE MEDICAL DEVICE

(71) Applicant: Medtronic, Inc., Minneapolis, MN (US)

(72) Inventors: Amy E. Thompson-Nauman, Ham Lake, MN (US); Melissa G. T. Christie, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/815,518

(22) Filed: Jul. 27, 2022

(65) Prior Publication Data
US 2022/0409882 A1 Dec. 29, 2022

Related U.S. Application Data

(60) Continuation of application No. 16/214,882, filed on Dec. 10, 2018, now Pat. No. 11,433,232, which is a division of application No. 14/257,462, filed on Apr. 21, 2014, now abandoned.

(60) Provisional application No. 61/820,024, filed on May 6, 2013.

(51) Int. Cl.
*A61N 1/05* (2006.01)
*A61N 1/39* (2006.01)

(52) U.S. Cl.
CPC .............. *A61N 1/05* (2013.01); *A61N 1/057* (2013.01); *A61N 1/0573* (2013.01); *A61N 1/3956* (2013.01); *A61N 2001/0578* (2013.01); *A61N 2001/058* (2013.01)

(58) Field of Classification Search
CPC ..... A61N 1/05; A61N 2001/0578; A61B 8/00
See application file for complete search history.

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |
| 4,270,549 A | 6/1981 | Heilman |
| 4,280,510 A | 7/1981 | O'Neill |
| 4,291,707 A | 9/1981 | Heilman et al. |
| 4,437,475 A | 3/1984 | White |
| 4,512,351 A | 4/1985 | Pohndorf |
| 4,538,624 A | 9/1985 | Tarjan |
| 4,765,341 A | 8/1988 | Mower et al. |

(Continued)

FOREIGN PATENT DOCUMENTS

| | | |
|---|---|---|
| WO | 2001023035 A1 | 4/2001 |
| WO | 2004073506 A2 | 9/2004 |

OTHER PUBLICATIONS

US 5,690,647 A, 11/1997, Fogarty et al. (withdrawn)

(Continued)

*Primary Examiner* — Ahmed M Farah
*Assistant Examiner* — Naveed R. Kolia
(74) *Attorney, Agent, or Firm* — Shumaker & Sieffert, P.A.

(57) ABSTRACT

Anchoring mechanisms for an implantable electrical medical lead that is positioned within a substernal space are disclosed. The anchoring mechanisms fixedly-position a distal portion of the lead, that is implanted in the substernal space.

20 Claims, 7 Drawing Sheets

(56) References Cited

U.S. PATENT DOCUMENTS

| | | |
|---|---|---|
| 4,832,687 A | 5/1989 | Smith, III |
| 5,036,854 A | 8/1991 | Schollmeyer et al. |
| 5,125,904 A | 6/1992 | Lee |
| 5,176,135 A | 1/1993 | Fain et al. |
| 5,203,348 A | 4/1993 | Dahl et al. |
| 5,255,691 A | 10/1993 | Otten |
| 5,255,692 A | 10/1993 | Neubauer et al. |
| 5,273,053 A | 12/1993 | Pohndorf |
| 5,300,106 A | 4/1994 | Dahl et al. |
| 5,312,355 A | 5/1994 | Lee |
| 5,441,504 A | 8/1995 | Pohndorf et al. |
| 5,456,699 A | 10/1995 | Armstrong |
| 5,476,493 A | 12/1995 | Muff |
| 5,509,924 A | 4/1996 | Paspa et al. |
| 5,613,953 A | 3/1997 | Pohndorf |
| 5,944,732 A | 8/1999 | Raulerson et al. |
| 5,951,518 A | 9/1999 | Licata et al. |
| 6,032,079 A | 2/2000 | KenKnight et al. |
| 6,104,957 A | 8/2000 | Alo et al. |
| 6,122,552 A | 9/2000 | Tockman et al. |
| 6,159,198 A | 12/2000 | Gardeski et al. |
| 6,228,052 B1 | 5/2001 | Pohndorf |
| 6,324,414 B1 | 11/2001 | Gibbons et al. |
| 6,415,187 B1 | 7/2002 | Kuzma et al. |
| 6,445,954 B1 | 9/2002 | Olive et al. |
| 6,544,247 B1 | 4/2003 | Gardeski et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,868,291 B1 | 3/2005 | Bonner et al. |
| 6,887,229 B1 | 5/2005 | Kurth |
| 6,999,819 B2 | 2/2006 | Swoyer et al. |
| 7,033,326 B1 | 4/2006 | Pianca et al. |
| 7,069,083 B2 | 6/2006 | Finch et al. |
| 7,117,039 B2 | 10/2006 | Manning et al. |
| 7,195,637 B2 | 3/2007 | Mika |
| 7,218,970 B2 | 5/2007 | Ley et al. |
| 7,229,450 B1 | 6/2007 | Chitre et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,369,899 B2 | 5/2008 | Malinowski et al. |
| 7,389,134 B1 | 6/2008 | Karicherla et al. |
| 7,450,997 B1 | 11/2008 | Pianca et al. |
| 7,499,758 B2 | 3/2009 | Cates et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,736,330 B2 | 6/2010 | Bardy |
| 7,765,014 B2 | 7/2010 | Eversull et al. |
| 7,837,671 B2 | 11/2010 | Eversull et al. |
| 7,846,088 B2 | 12/2010 | Ness |
| 7,890,191 B2 | 2/2011 | Rutten et al. |
| 7,908,015 B2 | 3/2011 | Lazeroms et al. |
| 7,930,040 B1 | 4/2011 | Kelsch et al. |
| 7,983,765 B1 | 7/2011 | Doan |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,260,436 B2 | 9/2012 | Gerber et al. |
| 8,280,527 B2 | 10/2012 | Eckerdal et al. |
| 8,340,779 B2 | 12/2012 | Harris et al. |
| 8,355,786 B2 | 1/2013 | Malinowski |
| 8,386,052 B2 | 2/2013 | Harris et al. |
| 8,435,208 B2 | 5/2013 | Bardy |
| 8,442,620 B2 | 5/2013 | Silipo et al. |
| 8,452,421 B2 | 5/2013 | Thenuwara et al. |
| 8,478,424 B2 | 7/2013 | Tronnes |
| 8,478,426 B2 | 7/2013 | Barker |
| 8,594,809 B2 | 11/2013 | Yang et al. |
| 8,886,311 B2 | 11/2014 | Anderson et al. |
| 11,433,232 B2 | 9/2022 | Thompson-Nauman et al. |
| 2002/0049485 A1 | 4/2002 | Smits |
| 2002/0120294 A1 | 8/2002 | Kroll |
| 2003/0114908 A1 | 6/2003 | Flach |
| 2003/0220677 A1 | 11/2003 | Doan et al. |
| 2004/0059348 A1 | 3/2004 | Geske et al. |
| 2004/0102829 A1 | 5/2004 | Bonner et al. |
| 2004/0210293 A1 | 10/2004 | Bardy et al. |
| 2004/0230279 A1 | 11/2004 | Cates et al. |
| 2004/0230281 A1 | 11/2004 | Heil et al. |
| 2004/0230282 A1 | 11/2004 | Cates et al. |
| 2004/0236396 A1 | 11/2004 | Coe et al. |
| 2005/0049663 A1 | 3/2005 | Harris et al. |
| 2005/0131505 A1 | 6/2005 | Yokoyama |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0247753 A1 | 11/2006 | Wenger et al. |
| 2006/0253181 A1 | 11/2006 | Schulman et al. |
| 2007/0100409 A1 | 5/2007 | Worley et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0171376 A1 | 7/2009 | Burton et al. |
| 2009/0222021 A1 | 9/2009 | Chang |
| 2009/0259282 A1 | 10/2009 | Williams et al. |
| 2009/0259283 A1 | 10/2009 | Brandt et al. |
| 2009/0264780 A1 | 10/2009 | Schilling |
| 2009/0270962 A1 | 10/2009 | Yang et al. |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0094252 A1 | 4/2010 | Wengreen et al. |
| 2010/0012519 A1 | 5/2010 | Bonner et al. |
| 2010/0113963 A1 | 5/2010 | Smits et al. |
| 2010/0137879 A1 | 6/2010 | Ko et al. |
| 2010/0152747 A1 | 6/2010 | Padiy et al. |
| 2010/0152798 A1 | 6/2010 | Sanghera et al. |
| 2010/0211064 A1 | 8/2010 | Mahapatra et al. |
| 2010/0217298 A1 | 8/2010 | Bardy |
| 2010/0217301 A1 | 8/2010 | Bardy |
| 2010/0241185 A1 | 9/2010 | Mahapatra et al. |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0224680 A1 | 9/2011 | Barker |
| 2011/0224681 A1 | 9/2011 | McDonald |
| 2011/0257660 A1 | 10/2011 | Jones et al. |
| 2011/0125163 A1 | 11/2011 | Rutten et al. |
| 2012/0016377 A1 | 1/2012 | Geroy |
| 2012/0029335 A1* | 2/2012 | Sudam .............. A61N 1/05 600/374 |
| 2012/0078266 A1 | 3/2012 | Tyson, Jr. |
| 2012/0089153 A1 | 4/2012 | Chistopherson et al. |
| 2012/0097174 A1 | 4/2012 | Spotnitz et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2013/0041345 A1 | 2/2013 | Kilcoin et al. |
| 2013/0103049 A1 | 4/2013 | Bonde |
| 2013/0158564 A1 | 6/2013 | Harris et al. |
| 2013/0238067 A1 | 9/2013 | Baudino |
| 2014/0330248 A1 | 11/2014 | Thompson-Nauman et al. |
| 2014/0330287 A1 | 11/2014 | Thompson-Nauman et al. |

OTHER PUBLICATIONS

Avogadros Lab Supply Inc., Catalog; Scoopula with Beech Wood Handle, can be found on-line at http://www.avogadro-lab-supply.com/search.php, accessed Oct. 6, 2013, 1 page.

(56) References Cited

OTHER PUBLICATIONS

Baudoin et al., The Superior Epigastric Artery Does Not Pass Through Larrey's Space (Trigonum Sternocostale) Surgical Radial Anal(2003), 25: 259-262.

Bielefeld et al., "Thoracoscopic Placement of Implantable Cardioverter-Defibrillator Patch Leads in Sheep", Circulation; Nov. 1993, vol. 88, No. 5, Part 2; 5 pages.

Bolling et al., "Automatic Internal Cardioverter Defibrillator: A Bridge to Heart Transplantation", Heart Lung Transplantation, Abstract Only, Jul.-Aug. 1991, 1 page.

Cigna et al., A New Technique for Substernal Colon Transposition with A Breast Dissector: Report of 39 Cases, Journal of Plastic, Reconstructive and Aesthetic Surgery, 2006:59, 4 pages.

Damiano, "Implantation of Cardioverter Defibrillators in the Post-Sternotomy Patient", The Annals of Thoracic Surgery, 1992; 53: pp. 978-983.

Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.

Frame et al., "Long-Term Stability of Defibrillation Thresholds with Intrapericardial Defibrillator Patches", Pacing and Clinical Electrophysiology, Jan. 1993, Part II, vol. 16, 6 pages.

Ganapathy et al., "Implantable Device to Monitor Cardiac Activity with Sternal Wires," Pace, vol. 37, Dec. 2014, 11 pages.

Guenther et al., "Substernal Lead Implantation: A Novel Option to Manage DFT Failsure in S-ICD patients," Clinical Research Cardiology, Published On-line Oct. 2, 2014, 3 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

Haydin et al., "Subxiphoid Approach to Epicardial Implantation of Implantable Cardioverter Defibrillators in Children", PACE, vol. 36, Aug. 2013, 5 pages.

Preliminary Report on Patentability from International Application No. PCT/US2014/035774, dated Nov. 10, 2015, 7 pp.

Search Report and Written from Application No. PCT/US2014/035774, dated Aug. 21, 2014, 10 pp.

Karwande et al., Bilateral Anterior Thoracotomy for Automatic Implantable Cardioverter Defibrillator Placement in Patients with Previous Sternotomy, The Annals of Thoracic Surgery; Oct. 1992; 54(4); 3 pages.

Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.

Lemmer, "Defibrillator Patch Constriction, Letter to the Editor", The Annals of Thoracic Surgery, 1996, 1 page.

Medtronic, Inc., 6996SQ Subcutaneous, Unipolar Lead with Defibrillation Coil Electrode, Technical Manual, May 10, 2002, 22 pp.

Medtronic, Inc., 6996T Tunneling Tool, Technical Manual, 12 pp. (2011). Applicant points out in accordance with MPEP 609.04(a) that the 2011 year of publication is sufficiently earlier than the effective U.S. filing date of the present application, and any foreign pIiority date that the paIticular month of publication is not in issue.

Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.

Molina et al, "An Epicardial Subxiphoid Implantable Defibrillator Lead: Superior Effectiveness After Failure of SIndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.

Obadia et al., "Thoracoscopic Approach to Implantable Cardioverter Defibrillator Patch Electrode Implantation", Pacing and Clinical Electrophysiology; Jun. 1996; vol. 19; 6 pages.

Obadia, et al., "New Approach for Implantation of Automatic Defibrillators Using Videothoracoscopy", Journal Ann Cardiel Angeiol (Paris); Sep. 1994; 43 (7) Abstract Only, 1 page.

Pebax Product Brochure, accessed from http://www.pebax.com/export/sites/pebax/.content/medias/downloads/literature/pebax-product-range-brochure.pdf on or before Aug. 17, 2014, archived at https://web.archive.org/web/20151223131256/http://www.pebax.com/export/sites/pebax/.content/medias/downloads/literature/pebax-product-range-brochure.pdf on Dec. 23, 2015, 14 pp.

Piccione, et al., "Erosion of ExtrapericardialImplantable Cardioverter Defibrillator Patch Through the Gastic Fundus with Fistulous Tract Information", Cardiology in Review; 2006; 14, e21-e23 pages.

Prosecution History from U.S. Appl. No. 14/257,462, dated Mar. 1, 2017 through Nov. 19, 2018, 88 pp.

Prosecution History from U.S. Appl. No. 16/214,882, now issued U.S. Pat. No. 11,433,232, dated Mar. 10, 2021 through May 4, 2022, 93 pp.

Quigley et al., "Migration of an Automatic Implantable Cardioverter-Defibrillator Patch Causing Massive Hemothorax", Journal Texas Heart Institute, Nov. 1, 1996; vol. 23, 4 pages.

Shapira, et al., A Simplied Method for Implantation of Automatic Cardioverter Defibrillator in Patients with Previous Cardiac Surgery, Pacing and Clinical Electrophysiology, Part I, Jan. 1993, vol. 16; 6 pages.

Steinke et al., Subepicardial Infarction, Myocardial Impression, and Ventricular Penetration by Sutureless Electrode and Leads, Chest; 70: Jul. 1, 1976, 2 pages.

Tung et al., "Minimal Invasive Extra Cardiac Placement of High Voltage Defibrillator Leads," Poster 3: S200 Abstract, PO-3-4; St. Paul Hospital, Vancouver, British Columbia, Canada, Oct. 2007, 1 pp.

Tung et al., "Minimal Invasive Extra Cardiac Placement of High Voltage Defibrillator Leads," Poster S200 Abstract, PO-3-4; St. Paul Hospital, Vancouver, British Columbia, Canada, Oct. 2007, 1 pp.

Vyhmeister et al., "Simple Approach for Extrapericardial Placement of Defibrillator Patches via Median Sternotomy", The Annals of Thoracic Surgery; 1994; 57:4 pages.

* cited by examiner

DEVICES AND TECHNIQUES FOR ANCHORING AN IMPLANTABLE MEDICAL DEVICE

CROSS-REFERENCE TO RELATED APPLICATIONS

This application is a continuation of U.S. patent application Ser. No. 16/214,882, entitled "DEVICES AND TECHNIQUES FOR ANCHORING AN IMPLANTABLE MEDICAL DEVICE" and filed on Dec. 10, 2018, which is a divisional of U.S. patent application Ser. No. 14/257,462, entitled "DEVICES AND TECHNIQUES FOR ANCHORING AN IMPLANTABLE MEDICAL DEVICE" and filed on Apr. 21, 2014, which claims the benefit of priority from U.S. Provisional Application Ser. No. 61/820,024, entitled "DEVICES AND TECHNIQUES FOR ANCHORING AN IMPLANTABLE MEDICAL DEVICE," and filed on May 6, 2013, the entire content of each of which is incorporated herein by reference.

FIELD OF THE INVENTION

The present application relates to implantable medical devices. In particular, methods, techniques devices are disclosed for anchoring implantable medical leads.

BACKGROUND OF THE INVENTION

Electrical stimulation of body tissue and organs is often used as a method of treating various conditions. Such stimulation is generally delivered by means of electrical contact between a pulse generator device and a target site via one or more implantable medical electrical leads connected to the pulse generator device; implantable leads typically include one or more stimulation electrodes joined to a distal portion of the lead, which are positioned and anchored in proximity to the target site.

In patients at high risk of ventricular fibrillation, the use of an implantable cardioverter defibrillator (ICD) system has been shown to be beneficial. An ICD system includes an ICD, which is a small battery powered electrical shock device, may include an electrical housing, or can electrode, that is coupled to one or more implantable medical leads that are implanted within the heart. If an arrhythmia is sensed, the ICD may send a pulse via the implantable leads to shock the heart and restore its normal rhythm. Owing to the inherent surgical risks in attaching and replacing implantable leads directly within or on the heart, methods have been devised to achieve a similar effect to that of a transvenous ICD system that is connected directly to the heart without placing implantable leads within the heart or attaching the leads directly to the heart.

Subcutaneous implantable cardioverter-defibrillator (SubQ ICD) systems have been devised to deliver electrical impulses to the heart by the use of one or more implantable leads that are placed subcutaneously on the torso. In order to effectively electrically stimulate the heart, the distal end of the implantable lead may be oriented longitudinally spanning from approximately the xiphoid to the high sternal area.

Various implantable medical lead structures and methods for positioning and anchoring lead electrodes in proximity to target sites have been developed over the years. New structures and methods are necessary to anchor lead electrodes for emerging therapy delivery requirements.

SUMMARY

Aspects in accordance with principles of the present invention relate to an implantable medical electrical lead for applying electrical stimulation to bodily tissue. The implantable lead is adapted to be introduced through an access point adjacent to the sternum and a distal portion is navigated into the substernal space. With this in mind, the implantable lead includes a lead body and an anchoring assembly. The lead body has a proximal section adapted to be electronically coupled to a power source and a distal section forming at least one exposed electrode surface.

In accordance with embodiments of the disclosure, the anchoring assembly may be located along a length of the lead body that is configured to be located within the substernal space, such as at or near the distal lead end. In other embodiments, the anchoring assembly may be located along a length of the lead body that is configured to be located at or near the access point into the substernal space.

Other aspects of the disclosure relate to a method of anchoring an implantable lead system. The method comprises subcutaneously advancing the lead to an access point into a substernal space of a patient, navigating a distal end of the lead to an implantation site within the substernal space, placing the distal end of the lead within the substernal space, orienting a fixation element in a pre-determined direction relative to the substernal space, and fixedly-securing a segment of the lead at the access point with a fixation element that secures the lead at an intersection between the subcutaneous space and the substernal space.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The disclosure describes techniques, components, assemblies, and methods for anchoring a lead in a patient's substernal space or extra-pericardium, with the lead being attachable to a subcutaneously implanted medical device. A distal end of the lead is positioned at a target implant site and anchored therein.

In this disclosure, "substernal space" refers to the region defined by the undersurface between the sternum and the body cavity, but not including the pericardium. In other words, the region is posterior to the sternum and anterior to the ascending aorta. The substernal space may alternatively be referred to by the terms "retrosternal space" or "mediastinum" or "infrasternal" as is known to those skilled in the art and includes the region referred to as the anterior mediastinum. The substernal space may also include the anatomical region described in Baudoin, Y. P., et al., entitled "The superior epigastric artery does not pass through Larrey's space (trigonum sternocostale)." *Surg. Radiol. Anat.* 25.3-4 (2003): 259-62 as Larrey's space. For ease of description, the term substernal space will be used in this disclosure, it being understood that the term is interchangeable with any of the other aforementioned terms.

In this disclosure, the term "extra-pericardial" space refers to region around the outer heart surface, but not within the pericardial sac/space. The region defined as the extra-pericardial space includes the gap, tissue, bone, or other anatomical features around the perimeter of, and adjacent to the pericardium.

In this specification, "anchor" means to fix a position of an object relative to tissue to minimize movement of the object relative to the tissue. Thus, although there may be small movements of the object relative to the tissue, arising for example from body movements of the patient that give rise to small deflections of the object within the tissue, the object is nevertheless "anchored" in the tissue. It is to be understood that features of the various exemplary embodiments described herein may be combined with each other, unless specifically noted otherwise.

Figure 1A:
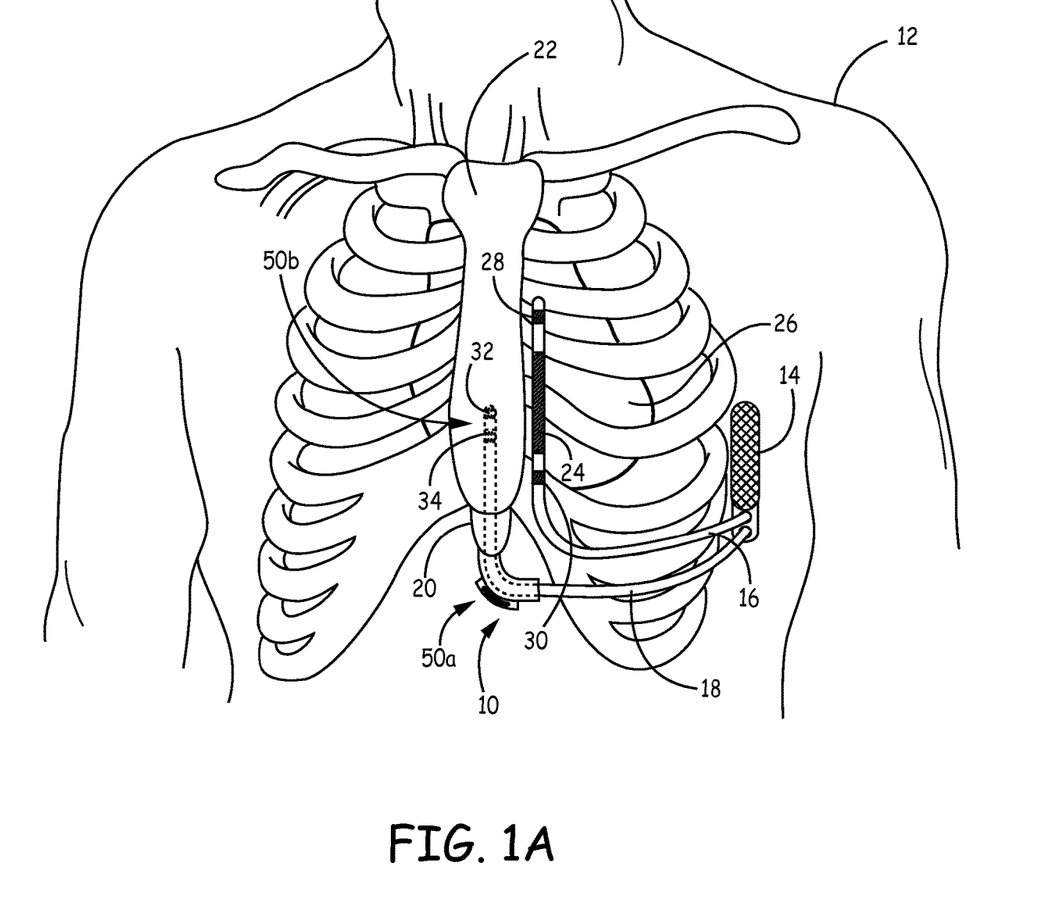
FIG. 1A is a front view of a patient implanted with implantable cardiac system.
Figure 1B:
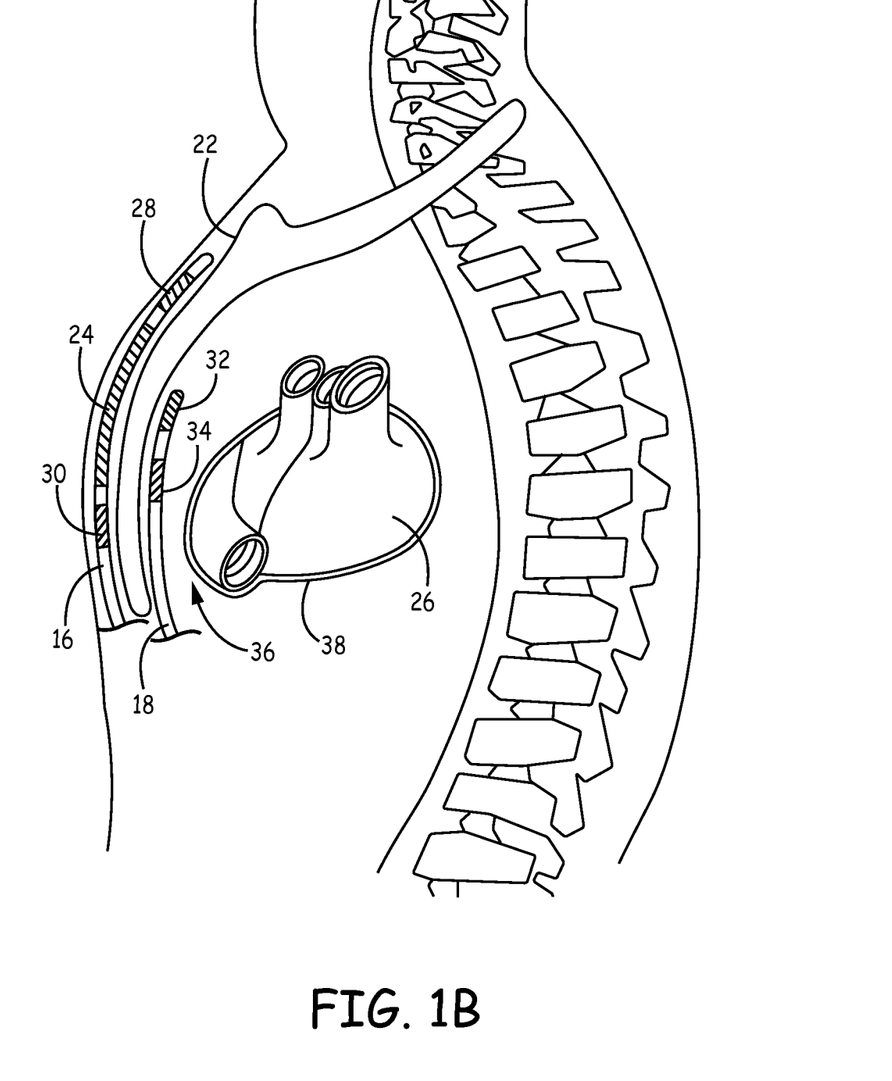
FIG. 1B is a side view the patient implanted with implantable cardiac system 10.
Figure 1C:
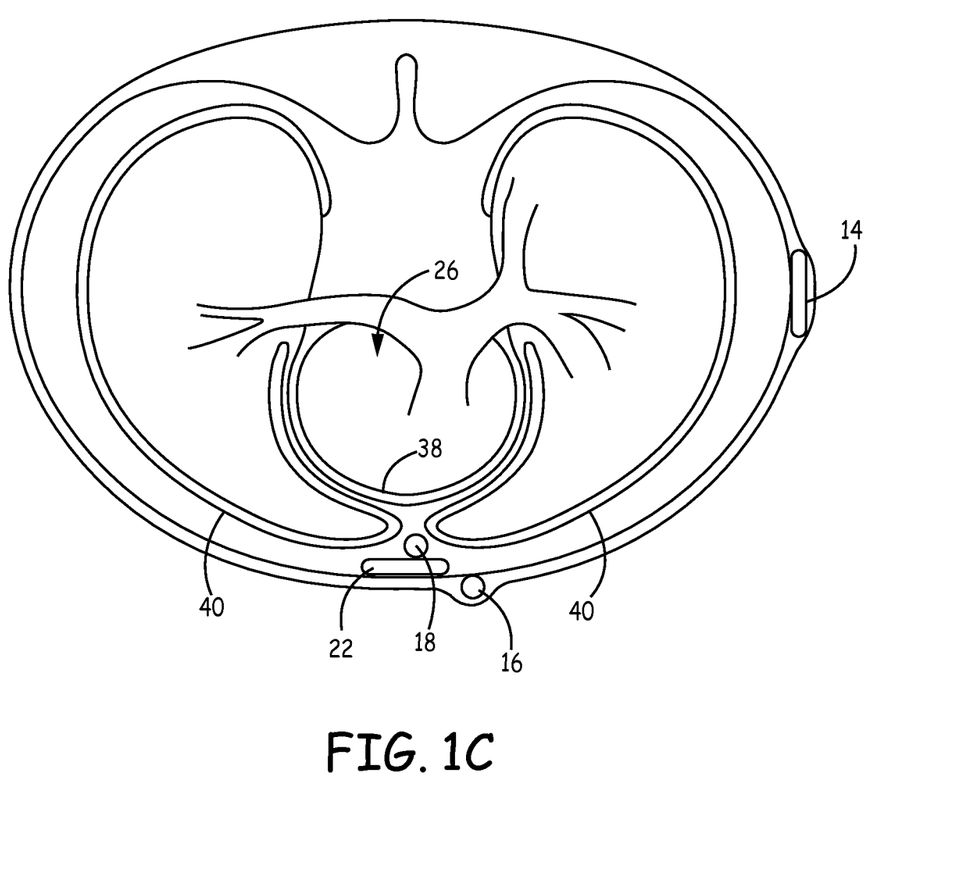
FIG. 1C is a transverse view of the patient implanted with implantable cardiac system.

FIGS. 1A-C are conceptual diagrams of a patient 12 implanted with an example implantable cardiac system 10. FIG. 1A is a front view of patient 12 implanted with implantable cardiac system 10. FIG. 1B is a side view patient 12 with implantable cardiac system 10. FIG. 1C is a transverse view of patient 12 with implantable cardiac system 10.

Implantable cardiac system 10 includes an implantable cardiac defibrillator (ICD) 14 connected to a first lead 16 and a second lead 18. The first lead 16 and the second lead 18 may be utilized to provide an electrical stimulation therapy such as pacing or defibrillation. For example, lead 16 may provide defibrillation therapy while lead 18 may provide pacing therapy, or vice versa, while in other embodiments, both lead 16 and lead 18 may provide pacing therapy or defibrillation therapy. In the example illustrated in FIGS. 1A-C ICD 14 is implanted subcutaneously on the left midaxillary of patient 12. ICD 14 may, however, be implanted at other subcutaneous locations on patient 12 as described later.

Lead 16 includes a proximal end that is connected to ICD 14 and a distal end that includes one or more electrodes. Lead 16 extends subcutaneously from ICD 14 toward xiphoid process 20. At a location near xiphoid process 20, lead 16 bends or turns and extends subcutaneously superior, substantially parallel to sternum 22. The distal end of lead 16 may be positioned near the second or third rib. However, the distal end of lead 16 may be positioned further superior or inferior depending on the location of ICD 14 and other factors. Although illustrated as being offset laterally from and extending substantially parallel to sternum 22 in the example of FIGS. 1A-C, lead 16 may be implanted over sternum 22, offset from sternum 22, but not parallel to sternum 22 (e.g., angled lateral from sternum 22 at either the proximal or distal end).

Lead 16 includes a defibrillation electrode 24, which may include an elongated coil electrode or a ribbon electrode, toward the distal end of lead 16. Lead 16 is placed such that a therapy vector between defibrillation electrode 24 and a housing or can electrode of ICD 14 is substantially across the ventricle of heart 26.

Lead 16 may also include one or more sensing electrodes, such as sensing electrodes 28 and 30, located toward the distal end of lead 16. In the example illustrated in FIGS. 1A-C, sensing electrode 28 and 30 are separated from one another by defibrillation electrode 24. ICD 14 may sense electrical activity of heart 26 via a combination of sensing vectors that include combinations of electrodes 28 and 30 and the housing or can electrode of ICD 14. For example, ICD 14 may obtain electrical signals sensed using a sensing vector between electrodes 28 and 30, obtain electrical signals sensed using a sensing vector between electrode 28 and the conductive housing or can electrode of ICD 14, obtain electrical signals sensed using a sensing vector between electrode 30 and the conductive housing or can electrode of ICD 14, or a combination thereof. In some instances, ICD 14 may even sense cardiac electrical signals using a sensing vector that includes defibrillation electrode 24.

Lead 18 includes a proximal end that is connected to ICD 14 and a distal end that includes one or more electrodes. Lead 18 extends subcutaneously from ICD 14 toward xiphoid process 20. At a location near xiphoid process 20 lead 18 bends or turns and extends superior upward in the substernal space. In one example, lead 18 may be placed in the mediastinum 36 and, more particularly, in the anterior mediastinum. The anterior mediastinum is bounded laterally by pleurae 40, posteriorly by pericardium 38, and anteriorly by sternum 22. Lead 18 may be implanted within the mediastinum such that one or more electrodes 32 and 34 are located over a cardiac silhouette of the ventricle as observed via fluoroscopy. In the example illustrated in FIGS. 1A-C, lead 18 is located substantially centered under sternum 22. In other instances, however, lead 18 may be implanted such that it is offset laterally from the center of sternum 22. Although described herein as being implanted in the substernal space, the mediastinum, or the anterior mediastinum, lead 18 may be implanted in other extra-pericardial locations.

Lead 18 includes electrodes 32 and 34 located near a distal end of lead 18. Electrodes 32 and 34 may comprise ring electrodes, hemispherical electrodes, coil electrodes, helical electrodes, ribbon electrodes, or other types of electrodes, or combination thereof. Electrodes 32 and 34 may be the same type of electrodes or different types of electrodes. In the example illustrated in FIGS. 1A-C electrode 32 is a hemispherical electrode and electrode 34 is a ring or coil electrode.

ICD 14 may deliver pacing pulses to heart 26 via a pacing or therapy vector that includes any combination of one or both of electrodes 32 and 34 and a housing electrode or can electrode of ICD 14. For example, ICD 14 may deliver pacing pulses using a pacing or therapy vector between electrodes 32 and 34, deliver pacing pulses using a pacing or therapy vector between electrodes 32 and the conductive housing or can electrode of ICD 14, deliver pacing pulses using a pacing or therapy vector between electrodes 34 and the conductive housing or can electrode of ICD 14, or a combination thereof. In some instances, ICD 14 may deliver pacing therapy via a therapy vector between one of electrode 32 (or electrode 34) and defibrillation electrode 24. In still further instances, ICD 14 may deliver pacing therapy via a therapy vector between one of electrode 32 (or electrode 34)

and one of sensing electrodes 28 or 30. ICD 14 may generate and deliver the pacing pulses to provide anti-tachycardia pacing (ATP), bradycardia pacing, post shock pacing, or other pacing therapies or combination of pacing therapies. In this manner, ATP therapy or post shock pacing (or other pacing therapy) may be provided in an ICD system without entering the vasculature or the pericardial space, nor making intimate contact with the heart.

ICD 14 may generate and deliver pacing pulses with any of a number of amplitudes and pulse widths to capture heart 26. The pacing thresholds of heart 26 when delivering pacing pulses substernally using lead 18 may depend upon a number of factors, including location of electrodes 32 and 34, location of ICD 14, physical abnormalities of heart 26 (e.g., pericardial adhesions), or other factors. The pacing thresholds needed to capture heart 26 tend to increase with shorter pulse widths. In the case of ATP, ICD 14 may deliver pacing pulses having longer pulse widths than conventional ATP pulses to reduce the amplitude of the pacing pulses. For example, ICD 14 may be configured to deliver pacing pulses having pulse widths or durations of greater than or equal to one (1) millisecond. In another example, ICD 14 may be configured to deliver pacing pulses having pulse widths or durations of greater than or equal to ten (10) milliseconds. In a further example, ICD 14 may be configured to deliver pacing pulses having pulse widths or durations of greater than or equal to fifteen (15) milliseconds. In yet another example, ICD 14 may be configured to deliver pacing pulses having pulse widths or durations of greater than or equal to twenty (20) milliseconds. Depending on the pulse widths, ICD 14 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. Typically the lower amplitudes require longer pacing widths as illustrated in the experimental results. Reducing the amplitude of pacing pulses delivered by ICD 14 reduces the likelihood of extracardiac stimulation.

ICD 14 may sense electrical activity of heart 26 via a combination of sensing vectors that include combinations of electrodes 32 and 34 and the housing or can electrode of ICD 14. For example, ICD 14 may obtain electrical signals sensed using a sensing vector between electrodes 32 and 34, obtain electrical signals sensed using a sensing vector between electrode 32 and the conductive housing or can electrode of ICD 14, obtain electrical signals sensed using a sensing vector between electrode 34 and the conductive housing or can electrode of ICD 14, or a combination thereof. In some instances, ICD 14 may sense electrical activity of heart 26 via a sensing vector between one of electrode 32 (or electrode 34) and electrodes 24, 28 and 30 of lead 16. ICD 14 may deliver the pacing therapy as a function of the electrical signals sensed via the one or more of the sensing vectors of lead 18. Alternatively or additionally, ICD 14 may deliver the pacing therapy as a function of the electrical signals sensed via one or more of the sensing vectors of lead 16.

ICD 14 also analyzes the sensed electrical signals from one or more of the sensing vectors of lead 18 and/or one or more of the sensing vectors of lead 16 to detect tachycardia, such as ventricular tachycardia or ventricular fibrillation. In some instances, ICD 14 delivers one or more ATP therapies via the one or more pacing or therapy vectors of lead 18 in response to detecting the tachycardia in an attempt to terminate the tachycardia without delivering a defibrillation shock. If the one or more ATP therapies are not successful or it is determined that ATP therapy is not desired, ICD 14 may deliver one or more defibrillation shocks via defibrillation electrode 24 of lead 16.

The configuration described above in FIGS. 1A-1C is directed to providing ventricular pacing via lead 18. In situations in which atrial pacing is desired in addition to or instead of ventricular pacing, lead 18 may be positioned further superior. A pacing lead configured to deliver pacing pulses to both the atrium and ventricle may have more electrodes. For example, the pacing lead may have one or more electrodes located over a cardiac silhouette of the atrium as observed via fluoroscopy and one or more electrodes located over a cardiac silhouette of the ventricle as observed via fluoroscopy. A pacing lead configured to deliver pacing pulses to only the atrium may, for example, have one or more electrodes located over a cardiac silhouette of the atrium as observed via fluoroscopy. In some instances, two substernal pacing leads may be utilized with one being an atrial pacing lead implanted such that the electrodes are located over a cardiac silhouette of the atrium as observed via fluoroscopy and the other being a ventricle pacing lead being implanted such that the electrodes are located over a cardiac silhouette of the ventricle as observed via fluoroscopy.

ICD 14 may include a housing that forms a hermetic seal that protects components of ICD 14. The housing of ICD 14 may be formed of a conductive material, such as titanium. ICD 14 may also include a connector assembly (also referred to as a connector block or header) that includes electrical feedthroughs through which electrical connections are made between conductors within leads 16 and 18 and electronic components included within the housing. As will be described in further detail herein, housing may house one or more processors, memories, transmitters, receivers, sensors, sensing circuitry, therapy circuitry and other appropriate components. Housing 34 is configured to be implanted in a patient, such as patient 12.

Leads 16 and 18 include a lead body that includes one or more electrodes located near the distal lead end or elsewhere along the length of the lead body. The lead bodies of leads 16 and 18 also contain one or more elongated electrical conductors (not illustrated) that extend through the lead body from the connector assembly of ICD 14 provided at a proximal lead end to one or more electrodes of leads 16 and 18. The lead bodies of leads 16 and 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of leads 16 and 18 may engage with respective ones of electrodes 24, 28, 30, 32, and 34. In one example, each of electrodes 24, 28, 30, 32, and 34 is electrically coupled to a respective conductor within its associated lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, 30, 32, and 34 and transmit sensed electrical signals from one or more of electrodes 24, 28, 30, 32, and 34 to the sensing module within ICD 14.

The lead 18 further includes one or more anchoring mechanisms that are positioned along the length of the lead body. The anchoring mechanisms affix the lead 18 that is implanted in a substernal space in a fixed location to prevent dislodging of the lead 18 once it is implanted. For example, the lead 18 may be anchored at one or more locations situated between the distal lead end positioned within the substernal space of patient 12 and a point along the length of the portion of the lead body at or near the insertion point of the lead body into the substernal space. The one or more anchoring mechanism(s) may either engage cartilage, bone, fascia, muscle or other tissue of patient 12 or may simply be wedged therein to affix the lead under the sternum to prevent excessive motion or dislodgment. Furthermore, it should be understood that various anchoring mechanisms described in this disclosure may additionally be utilized for delivery of a stimulation therapy as is known in the art.

In accordance with various embodiments, this disclosure describes anchoring mechanisms that are integrated into the lead body. In such embodiments, a portion or segment of the lead body may be formed with materials that function to encase conductors and other elements internal to the lead while also anchoring the lead within the implant environment.

In alternative embodiments, anchoring mechanisms of the disclosure are described as discrete elements that may be formed in line with the lead body. In some embodiments, the discrete components may be provided in a fixedly-secured relationship to the lead body. In other embodiments, the anchoring mechanism may be detachedly coupled in a sliding relationship over the lead body.

The anchoring mechanisms may include a passive anchoring mechanism, an active anchoring mechanism or a combination of both. In one embodiment, the anchoring mechanism is coupled along a length of the lead body and it may also function as an electrically active element. Examples of passive anchoring mechanisms include flanges, disks, pliant tines, flaps, porous structures such as a mesh-like element that facilitates tissue growth for engagement, bio-adhesive surfaces (such as those described in U.S. Pat. No. 8,594,809, which is incorporated herein by reference in its entirety), and/or any other non-piercing elements. Examples of active anchoring mechanisms may include rigid tines, prongs, burbs, clips, screws, and/or other projecting elements that pierce and penetrate into tissue to anchor the lead. As another example of an active anchoring mechanism, the lead may be provided with a side helix for engaging tissue. It is contemplated that any of these anchoring mechanisms will be formed from materials including shape memory alloys such as Nitinol to facilitate the deployment of the lead.

The various examples of the anchoring mechanisms may be deployable. As such, the anchoring mechanism assumes a first state during maneuvering of the lead (during which time the lead is disposed within a lumen of a delivery system or over a guidewire or stylet) to the desired implant location. Subsequently, the anchoring mechanism assumes a second state following the release of the lead from the delivery system into the substernal space to thereby anchor the distal end portion of the lead body relative to the adjacent tissue.

In addition or alternatively, the lead may be anchored through a suture that fixedly-secures the lead to the cartilage, musculature, tissue or bone at the access point into the substernal space of patient 12. In some embodiments, the suture may be sewn to the patient 12 through pre-formed suture holes to the patient 12.

As shown in FIG. 1A, an anchoring mechanism 50a or anchoring mechanism 50b (collectively "anchoring mechanism 50") may be provided along the lead body to couple the lead 18 at an access point through which the distal end of the lead 18 is inserted into the substernal space. The access point is any location that provides access into the substernal space. In one exemplary embodiment, the access point is adjacent to or below the xiphoid process (also referred to as "subxiphoid"). The access point may also be at the notch (not shown) that connects the xiphoid process to the sternum. In other embodiments, the substernal space may also be accessed through the manubrium.

An example of the anchoring mechanism 50a includes a suture or clip or other fastener that anchors the lead body to the patient 12. The anchoring mechanism 50a embodied as a fastener may be coupled directly to the lead body or to a suture sleeve such as that described in U.S. Pat. No. 5,273,053, issued to Pohndorf and incorporated herein by reference in its entirety. The anchoring mechanism 50a is fixedly-coupled to cartilage, musculature, tissue or bone at the entry point into the substernal space at or near the access point at which site the body of the lead 18 transitions from the subcutaneous tissue into the substernal space of patient 12.

Figure 8:
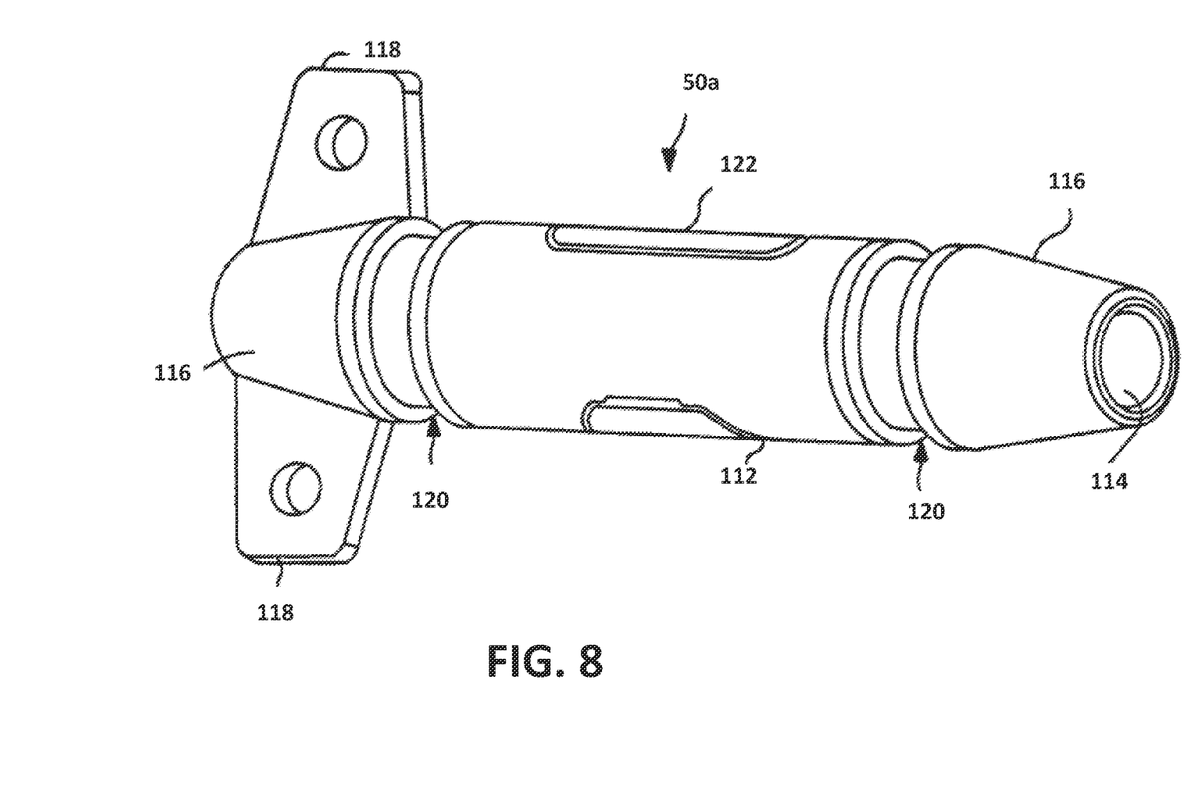
FIG. 8 depicts an embodiment of a lead anchoring mechanism of a lead of the implantable cardiac system.

As described in U.S. Pat. No. 5,273,053 and illustrated in FIG. 8, anchoring mechanism 50a may be a sleeve comprising a main sleeve body 112, e.g., a cylindrical body, having a first, longitudinal throughbore 114 therethrough, e.g., a cylindrical throughbore, for receiving the lead. Cylindrical body 112 may be made of hard, injection-molded plastic. Anchoring mechanism 50a may include endpieces 116, which may optionally be provided with radially-projecting fins or tabs 118 that may be formed of silicone rubber. Each of endpieces 116 may define at least one circumferential groove 120 on its outer surface, for allowing anchoring mechanism 50a to be sutured to a vein or underlying tissue. Anchoring mechanism 50a may include a pushbutton-type locking mechanism 122. Actuation of pushbutton 122 may enable anchoring mechanism 50a to slide along a length of lead 18. It should be understood that anchoring mechanism 50a sliding along a length of lead 18 is equivalent to lead 18 sliding relative to anchoring mechanism 50a. For example, anchoring mechanism 50a may be fixed in space (e.g., secured to tissue of patient 12), and lead 18 may be advanced through throughbore 114 of anchoring mechanism 50a.

In an embodiment, the anchoring mechanism 50a that is positioned at the access point may further be formed to accommodate the curvature of the patient 12 anatomy. In other words, the body of the anchoring mechanism 50a embodied, for example as a suture sleeve, may be malleable or pre-shaped to conform to the bend angle of the site at which the lead 18 transitions from the subcutaneous tissue into the substernal space of patient 12. As such, the suture sleeve may include a segment having a preformed bend angle of approximately 90 degrees. Thus, the anchoring sleeve may be positioned partially in the subcutaneous tissue and partially within the substernal space. The anchoring sleeve may be coupled to the patient 12 at one or more points along the length of the anchoring sleeve.

The anchoring mechanism 50a may further be constructed to facilitate tissue in-growth for long-term fixation of the lead 18. To promote such tissue in-growth, the anchoring mechanism 50a may be formed having a multi-layer construction or having pores. In some embodiments, the anchoring mechanism 50a may be constructed having a cross-linked structure. In accordance with other embodiments, the materials for construction of the anchoring mechanism 50a having a multi-layer structure may include bio-absorbable materials which will degrade a short time after implant. The anchoring mechanism 50a may also include a collagen layer which has been pre-treated to promote the tissue growth.

An example of the anchoring mechanism 50b may include a fixation element that is disposed continuously or partially around the body of lead 18 to couple the lead 18 to the access point. The anchoring mechanism may be fixedly coupled to the lead or slidingly-disposed over the lead, such as the anchoring member described in U.S. Pat. No. 5,476,493 to Muff, which is configured to be movable axially along the length of the lead body, to facilitate positioning of the anchoring mechanism 50b at a point suitable for affixation to tissue adjacent to the xiphoid process. In other words, anchoring mechanism 50b may be disposed around the lead body in a sliding relationship to facilitate navigation and placement of the distal end of the lead into the substernal space and the subsequent movement of the anchoring mechanism 50b to the site for fixation.

In some embodiments, lead 18 further includes a reinforced distal end 36 that is formed to facilitate anchoring of the lead 18 within the substernal space. The reinforced distal end 36 of the lead 18 prevents flexing of the lead 18 responsive to body motions. The distal end 36 may be formed from a material having a greater stiffness coefficient relative to that of the material of the lead body, or with a coating, or a resilient member—such as a coil—coupled over the lead body, any of which is fabricated to impart stiffness to the distal end 36. The reinforced distal end 36 exhibits characteristics that eliminate or minimize the motion of the distal end of the lead. As such, the distal end 36 functions to anchor the lead 18 within the tissue of patient 12.

In addition, the reinforced distal end 36 may be constructed to facilitate tissue in-growth for long-term fixation of the lead 18. To promote such tissue in-growth, the distal end 36 may be formed having a multi-layer construction or having pores. In some embodiments, the distal end 36 may be constructed having a cross-linked structure. In accordance with other embodiments, the materials for construction of the distal end 36 having a multi-layer structure may include bio-absorbable materials which will degrade a short time after implant. The distal end 36 may also include a collagen layer which has been pre-treated to promote the tissue growth.

A backfilling process may be utilized to increase the stiffness coefficient of the reinforced distal end 36 relative other segments of the body of lead 18. For example, the lead 18 body may be formed with multiple insulative layers with the backfill material—such as a medical adhesive or additional material—being added to reinforce the distal end 36. In other embodiments, the reinforced distal end 36 may be formed with materials having an increased rigidity, relative to the rest of the lead body. For example, the reinforced distal end 36 may be fabricated from such materials as an ultra-high molecular density polyethylene, polyester or other high tensile strength fiber or plastic. In other examples, a lead body of lead 18 that is manufactured of relatively soft plastics of low tensile strength may be reinforced to provide a reinforced distal end 36 by increasing the layers of material used in the region of distal end 36.

The examples illustrated in FIGS. 1A-C are exemplary in nature and should not be considered limiting of the techniques described in this disclosure. In other examples, ICD 14, lead 16, and lead 18 may be implanted at other locations. For example, ICD 14 may be implanted in a subcutaneous pocket in the right chest. In this example, lead 16 may be extend subcutaneously from the device toward the manubrium of the sternum and bend or turn and extend subcutaneously inferiorly from the manubrium of the sternum, substantially parallel with the sternum and lead 18 may extend subcutaneously from the device toward the manubrium of the sternum to the desired location and bend or turn and extend substernally inferiorly from the manubrium of the sternum to the desired location.

In the example illustrated in FIG. 1, system 10 is an ICD system that provides pacing therapy. However, these techniques may be applicable to other cardiac systems, including cardiac resynchronization therapy defibrillator (CRT-D) systems, cardioverter systems, or combinations thereof.

In addition, it should be noted that system 10 may not be limited to treatment of a human patient. In alternative examples, system 10 may be implemented in non-human patients, e.g., primates, canines, equines, pigs, bovines, ovines, and felines. These other animals may undergo clinical or research therapies that may benefit from the subject matter of this disclosure.

Figure 2:
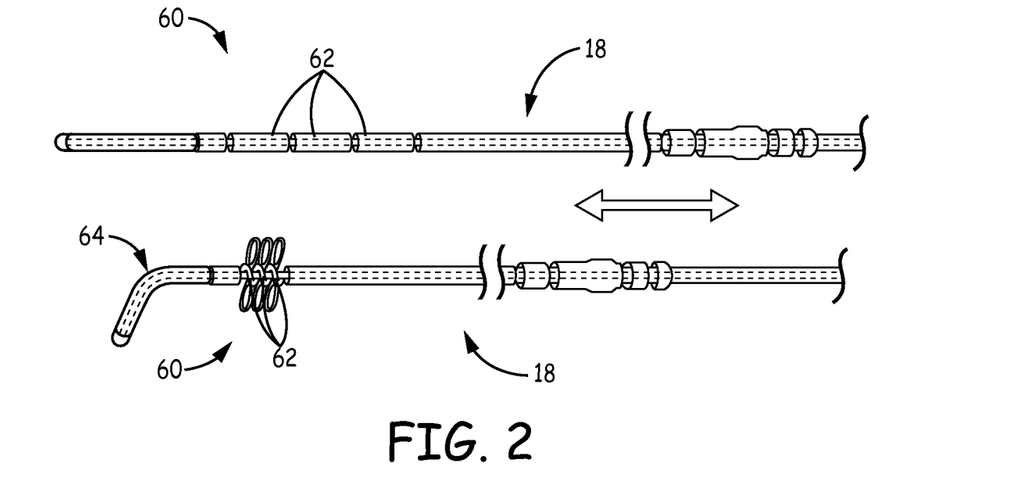
FIG. 2 depicts an embodiment of a lead anchoring mechanism of a lead of the implantable cardiac system.

FIG. 2 depicts a lead anchoring mechanism 60 that includes a plurality of struts 62 that are disposed over the lead 18 in a sliding relationship and are configured to expand from a collapsed configuration to an expanded configuration such that the plurality of struts 62 expand to press against tissue surrounding the implant location.

In one embodiment, the struts 62 may be displaced distally—relative to a mid-axis of the lead 18—by employing a deployment member (not shown) that causes both distal-ward movement and expansive displacement of the struts 62 into the expanded state. Other deployment mechanisms may include pneumatic activation (fluid or gas activated), or direct connection via rods, or any other type of proximally applied torque that causes force transfer to deploy the struts 62.

According to one exemplary embodiment, the lead anchoring mechanism 60 is made from a super-elastic material. The struts 62 may be formed from a tubular collar with material being removed to form two or more expandable struts 62.

The lead 18 in FIG. 2 further includes a canted distal portion 64. As illustrated, the body of lead 18 is pre-shaped to be canted at an angle in the range of 10 degrees to 90 degrees, relative to the remaining, proximal, portion of the lead body. The pre-shape canted distal portion 64 may be constructed by providing an inner layer having a shape memory material over this section of the lead body. During delivery of the lead body, the lead 18 may be positioned with a catheter or other delivery system that causes the canted distal portion 64 to be straightened. Therefore, the bias of the distal portion 64 is such that the introduction of a straight stylet into a center lumen of the lead body or the insertion of lead body into a guide catheter may cause the bend to be straightened. Upon insertion into the substernal space, the canted distal portion 64 permits the lead body to assume the pre-determined shape thereby causing the distal portion 64 to anchor to tissue within the substernal space.

Although the canted distal portion 64 is shown in conjunction with the anchoring mechanism 60, it should be noted that alternative embodiments of the lead 18 may simply include the canted distal portion 64 without the anchoring mechanism 60.

Figure 3:
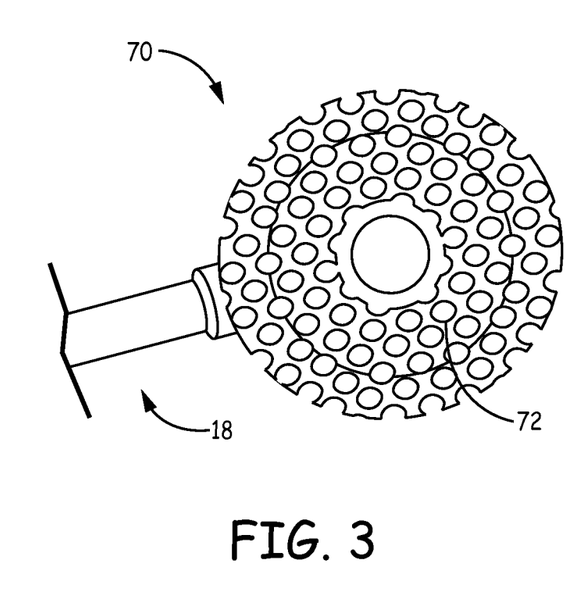
FIG. 3 depicts an embodiment of a lead anchoring mechanism of a lead of the implantable cardiac system.

In FIG. 3, an anchoring mechanism 70 is coupled to the distal end of the lead 18. The anchoring mechanism 70 may be configured as a flange or pad mounted to the distal end of the lead 18. The anchoring mechanism 70 includes a major surface 72 that is greater than a minor surface (not shown) that is perpendicular to the major surface. The major surface 72 is characterized by a width that is greater relative to the width of the minor surface. When coupled to the lead 18, the major surface is oriented in line with an imaginary axis of the body of lead 18 running continuously between the proximal end and the distal end. The cross-sectional profile of the anchoring mechanism 70 is dimensioned to be greater than a cross-sectional profile of the lead 18. For example, the anchoring mechanism 70 may be configured having a width that is greater than that of the lead 18 as viewed from a side perspective or side cross-section.

Electrode 32 may be attached to the lead 18 overlying a portion of lead anchoring mechanism 70. In this mounting configuration, the electrode 32 may be oriented to direct the field of the stimulation energy in a pre-determined direction at the implant location.

In one embodiment, anchoring mechanism 70 may include a mesh-like structure having pores that permit ingrowth of tissue that affixes to the anchoring mechanism. In other embodiments, the anchoring mechanism 70 may include a bioreactive adhesion layer (not shown) such as that described in the US Patent Application No. 2009/0270962, with the bioreactive adhesion layer being coupled to the surface of the anchoring mechanism 70. In such an embodiment, a cover (not shown) may be utilized to seal off the bioreactive adhesion layer from the external environment until the anchoring mechanism is situated at an appropriate implant site.

Figure 4:
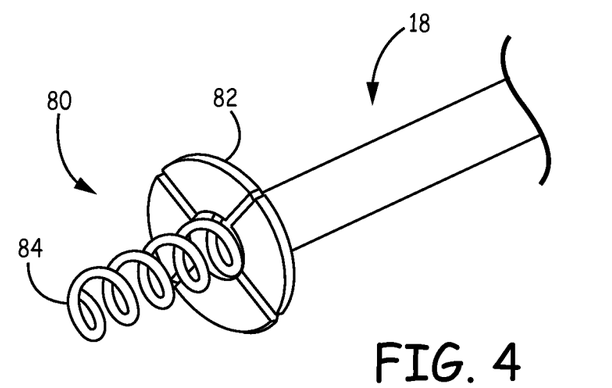
FIG. 4 depicts an embodiment of a lead anchoring mechanism of a lead of the implantable cardiac system.

FIG. 4 illustrates an anchoring mechanism 80 having a combination passive fixation element 82 and an active fixation element 84 coupled to the distal end of lead 18. The illustration depicts the fixation element 82 and fixation element 84 in an expanded or deployed configuration. The passive fixation element 82 may be a disk that expands radially relative to the width of the lead body to define a circumference that is larger than the circumference of the lead body. The anchoring mechanism 80 further illustrates active fixation element 84 that may be a helix that extends in axially from the distal end of the lead body and is configured for insertion into tissue. The fixation element 84 may be screwed out of the distal tip of the lead body, for example, through a rotational force that is imparted by rotating the lead body.

Figure 5:
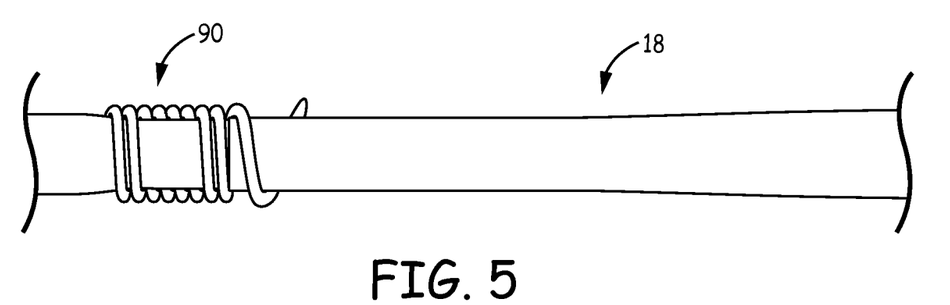
FIG. 5 depicts an embodiment of a lead anchoring mechanism of a lead of the implantable cardiac system.

FIG. 5 illustrates an anchoring mechanism 90 coupled along a length of the lead body. The anchoring mechanism 90 comprises a side helix that engages with tissue. The side helix may be formed as a coil wound over the lead body. Engagement of the tissue occurs through protrusion of the side helix in a direction that is perpendicular to an imaginary axis from the proximal to the distal end of the lead.

Figure 6:
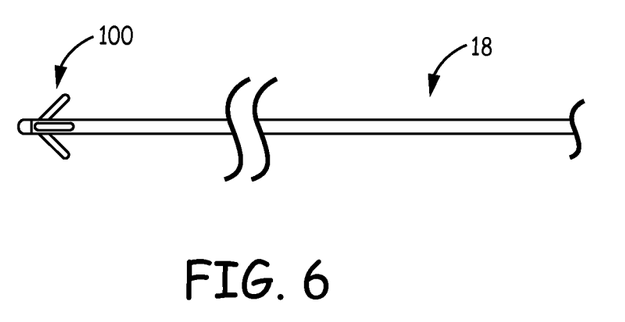
FIG. 6 depicts an embodiment of a lead anchoring mechanism of a lead of the implantable cardiac system.

FIG. 6 is a side view of anchoring mechanism 100 positioned at a proximal end of electrode 32 of a lead of a medical device according to an embodiment. The anchoring mechanism 100 is positioned proximal from the electrode 32 on the lead body of lead 18 and includes proximal tines that are formed of flexible or pliant material such as polymeric materials for example, as silicone rubber or polyurethane to passively fixate to tissue. In another embodiment, the tines may be formed of a rigid material such as titanium or PEEK for active fixation to the tissue. During deployment of the anchoring mechanism 100, the tines are folded such that the tine elements are retracted or constrained against the lead body. This may be accomplished by positioning the lead 18 within a lumen of a delivery system having a diameter smaller than the width defined by the expanded tines. Upon delivery to the proper location, the lead 18 is released from the delivery system allowing the tines to return to their extended position whereby they push against or pierce the tissue improving both acute and chronic fixation.

Figure 7:
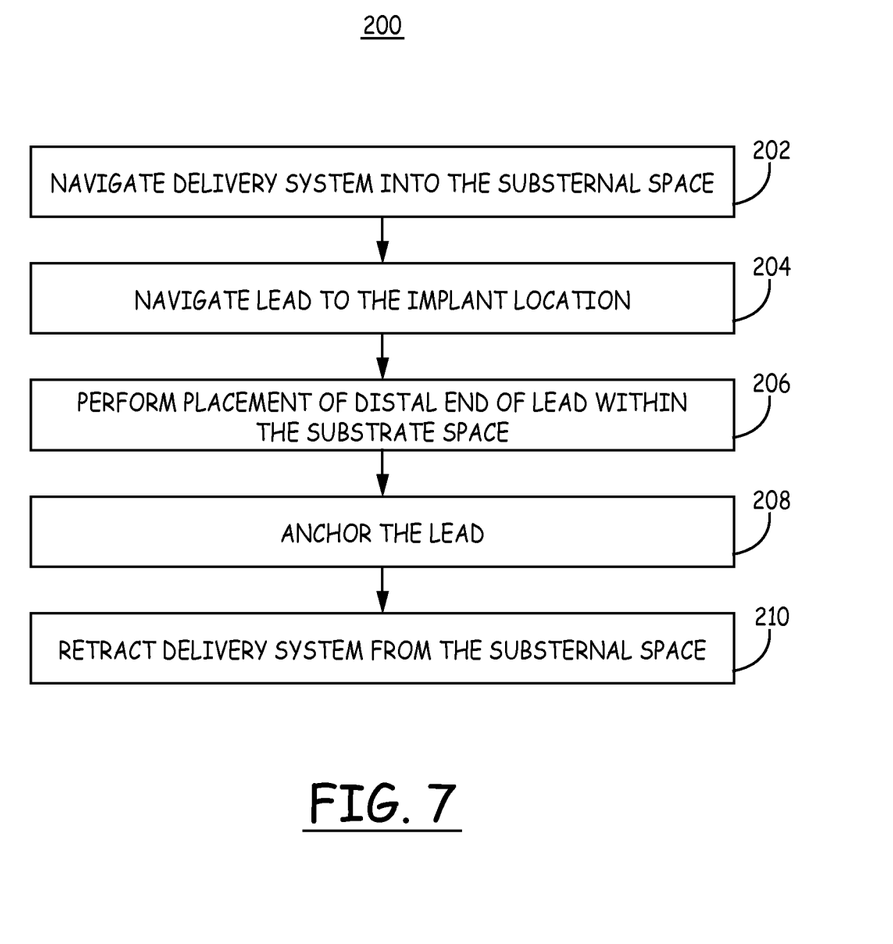
FIG. 7 is a flow diagram illustrating an exemplary method of implanting a lead according to an embodiment.

FIG. 7 is a flow diagram illustrating an exemplary method of implanting a lead according to an embodiment of the disclosure. In particular, the method involves implantation of a medical lead in a substernal space underneath the sternum and fixedly-securing the distal end of the lead to patient tissue. Lead 18 (FIGS. 1-6) comprises one example of such a medical lead that may be implanted in the substernal space.

The lead 18 is implanted in a region that is underneath the sternum and within the mediastinum space. The mediastinum space may include the region that is posterior to the sternum and anterior to the pericardial sac from the xiphoid to the manubrium and bounded laterally on the left and right by the internal thoracic arteries. A lead implanted in the substernal space may provide a stimulation therapy, such as a pacing therapy (including anti-tachy pacing, post-shock pacing, chronic pacing) or a defibrillation therapy or both.

A delivery system such as that disclosed in U.S. Patent Application No. 61/820,014, "Systems And Methods For Implanting A Medical Electrical Lead Within A Substernal Space" which is hereby incorporated by reference in its entirety, may be utilized to implant the lead. When used, the delivery system is navigated into the substernal space through an access point on the patient (202). The navigation of the delivery system to the appropriate location may be aided by various navigation aids discussed in the 61/820,014 application, including: a radiopaque marker that is visualized through fluoroscopy, signals obtained from the distal end of the delivery system body, and a directional indicator on the delivery system. Again, the access point may be any location on the tissue of the patient 12 where an incision is made to provide access into the substernal space.

At task 204, a distal end of the lead is navigated to the implantation site within the substernal space. The lead body may extend from a stimulation therapy generating device, such as device 14, that is positioned subcutaneously, such as at the left mid-axillary of the patient, and tunneled toward the xiphoid process. The navigation of the lead from the xiphoid process into the substernal space may be performed such that the distal end of the lead is directed toward the jugular notch from the xiphoid process in a generally axial direction.

The distal end of the lead is positioned within the substernal space at a location over a cardiac silhouette of the ventricle as observed via fluoroscopy. In particular, the electrodes may be oriented towards a target stimulation site (206). In one example, the desired orientation of the electrode may be achieved by orienting an anchoring mechanism that is coupled to the lead in a direction that causes the electrode to be positioned in a direction towards the target stimulation site. For example, the electrode may be formed integrally with an anchoring mechanism such as that described in FIG. 3. In this configuration, the movement, including rotational or longitudinal movement, of the anchoring mechanism triggers movement of the electrode in the corresponding direction which facilitates orientation of the electrode in the desired direction.

At task 208, the lead is anchored to tissue surrounding the implant environment. The lead may be anchored at the distal end, proximate to the distal end or any other location along the length of the lead between the access point into the xiphoid process and the distal end of the lead. In doing so, the portion of the lead within the substernal space is anchored to prevent dislodgment of the lead.

In some embodiments, the anchoring mechanism may be configured in a first retracted configuration during the navigation of the lead and re-configured into a second expanded configuration when the lead is released within the substernal space. In other embodiments, the anchoring mechanism is retracted from an interior portion of the lead. Additionally, the lead body may be sutured at or near the xiphoid process to fixedly couple the lead.

At task 210, the delivery system is retracted from the patient after the lead has been guided to the implant site.

As described herein, anchoring devices, systems and methods in accordance with various embodiments are provided that facilitate implantation and stabilization of a lead in the substernal space. In alternative implementations, the devices, systems and methods may be utilized for lead implantation and fixation in locations other than the substernal space including but not limited to the aforementioned extra-pericardial space.

Various examples have been described. It is contemplated that the features described in the different embodiments may be combined to create additional embodiments. All such disclosed and other examples are within the scope of the following claims.

What is claimed is:

1. An implantable medical system comprising:
   an implantable medical lead configured to be navigated from an access point of a patient to an implantation site within a substernal space of the patient, wherein the implantable medical lead comprises at least one electrode configured to be oriented within the substernal space relative to a heart of the patient; and
   an anchoring mechanism configured to be slidably disposed along a length of the implantable medical lead and positioned at the access point of the patient, the anchoring mechanism configured to:
      secure the implantable medical lead at the access point; and
      fixedly-secure the at least one electrode oriented relative to the heart at the implantation site.

2. The implantable medical system of claim 1, wherein the anchoring mechanism comprises a suture sleeve configured to:
   couple to a lead body of the implantable medical lead; and
   fixedly-couple to at least one of cartilage, musculature, tissue or bone at the access point.

3. The implantable medical system of claim 1, wherein the anchoring mechanism comprises a reinforcement member that is configured to prevent movement of the implantable medical lead responsive to a dislodgment force from the tissue at the implant location.

4. The implantable medical system of claim 1, wherein the anchoring mechanism is configured to orient at least one of the at least one electrode relative to a target stimulation therapy site that is not within the substernal space.

5. The implantable medical system of claim 1, wherein the anchoring mechanism comprises a flange having at least one major surface that is oriented in a parallel configuration with the length of the implantable medical lead.

6. The implantable medical system of claim 1, wherein a distal end of the implantable medical lead is configured to be tunneled through a pathway across subcutaneous tissue for insertion into the substernal space.

7. The implantable medical system of claim 1, wherein the anchoring mechanism comprises a porous structure.

8. The implantable medical system of claim 7, wherein the anchoring mechanism comprises an in-growth member having a substance configured to promote tissue growth for anchoring the implantable medical lead to tissue.

9. The implantable medical system of claim 1, wherein the anchoring mechanism is moveable along the length of the body during navigation of the implantable medical lead.

10. The implantable medical system of claim 1, wherein the anchoring mechanism comprises a passive fixator configured to engage tissue.

11. The implantable medical system of claim 1, wherein the anchoring mechanism comprises an active fixator configured to engage tissue.

12. The implantable medical system of claim 1, wherein the anchoring mechanism comprises a porous structure having pores for tissue engagement.

13. The implantable medical system of claim 1, wherein the anchoring mechanism comprises an electrically insulative material.

14. The implantable medical system of claim 1, wherein the anchoring mechanism comprises a polymeric material.

15. The implantable medical system of claim 1, wherein the anchoring mechanism comprises a plastic.

16. The implantable medical system of claim 1, wherein the anchoring mechanism comprises an elongate body having a longitudinal throughbore for receiving the implantable medical lead.

17. The implantable medical system of claim 16, wherein the elongate body is cylindrical.

18. The implantable medical system of claim 16, wherein the throughbore is cylindrical.

19. The implantable medical system of claim 16, wherein the anchoring mechanism comprises a plurality of radially projecting members.

20. A method comprising:
   navigating at least one electrode of an implantable medical lead from an access point of a patient to an implantation site within a substernal space of the patient, wherein navigating the implantable medical lead comprises orienting the at least one electrode within the substernal space relative to a heart of the patient; and
   fixedly-securing the at least one electrode of the implantable medical lead oriented relative to the heart at the implantation site using one or more anchoring mechanisms slidably disposed along a length of the implantable medical lead and positioned at the access point of the patient, wherein fixedly-securing comprises securing the implantable medical lead at the access point with at least one anchoring mechanism of the one or more anchoring mechanisms.

* * * * *